US007718213B1

(12) United States Patent
Scheer

(10) Patent No.: US 7,718,213 B1
(45) Date of Patent: May 18, 2010

(54) HOLDING DEVICE AND METHOD FOR COATING A SUBSTRATE

(76) Inventor: Ingo Werner Scheer, 6455 La Jolla Blvd., La Jolla, CA (US) 92037

( * ) Notice: Subject to any disclaimer, the term of this patent is extended or adjusted under 35 U.S.C. 154(b) by 514 days.

(21) Appl. No.: 11/644,267

(22) Filed: Dec. 23, 2006

Related U.S. Application Data

(60) Provisional application No. 60/776,522, filed on Feb. 24, 2006.

(51) Int. Cl.
*A61L 33/00* (2006.01)

(52) U.S. Cl. ......................... 427/2.24; 427/8; 427/2.25; 427/421.1; 427/424; 427/425; 427/427.3; 427/427.4; 427/427.5; 118/500

(58) Field of Classification Search ................ 118/500; 427/2.24
See application file for complete search history.

(56) References Cited

U.S. PATENT DOCUMENTS 3,206,135 A * 9/1965 Uncapher ................ 242/573.2
4,733,665 A 3/1988 Palmaz
6,572,644 B1 6/2003 Moein
6,605,154 B1 8/2003 Villareal
6,620,194 B2 9/2003 Ding
6,695,920 B1 * 2/2004 Pacetti et al. ................ 118/500
6,818,063 B1 * 11/2004 Kerrigan ..................... 118/500
2003/0207019 A1 * 11/2003 Shekalim et al. ........... 427/2.24
2004/0230298 A1 11/2004 Udipi
2005/0149177 A1 7/2005 Weber

FOREIGN PATENT DOCUMENTS

WO WO 2004008995 A2 1/2004
WO WO2004/037126 * 5/2004
WO WO 2004037126 A3 5/2004

* cited by examiner

*Primary Examiner*—Michael Barr
*Assistant Examiner*—Andrew Bowman

(57) ABSTRACT

A holding device and method is provided for efficiently applying a coating on the exterior surface of a tubular hollow body, while preventing coating application on the interior surface and coating defects. The holding device of the present invention comprises at least two structures contacting the inner surface of the tubular hollow body and extending to a portion where the structures are connected and rotary motion is induced to rotate the tubular hollow body. The structures are arranged and shaped so that an inner hollow section is formed in which excess coating material can accumulate.

17 Claims, 10 Drawing Sheets

HOLDING DEVICE AND METHOD FOR COATING A SUBSTRATE

CROSS-REFERENCE TO RELATED APPLICATIONS

This Application relates to and claims priority from commonly owned U.S. Provisional Patent Application Ser. No. 60/776,522, filed on Feb. 24, 2006.

FEDERALLY SPONSORED RESEARCH

Not Applicable

SEQUENCE LISTING OR PROGRAM

Not Applicable

BACKGROUND OF THE INVENTION

1. Field of Invention

This invention relates to a holding device and a method of coating hollow cylindrical objects using the device. More specifically, the present invention provides a holding device and a method of selectively and efficiently coating one or more hollow cylindrical objects, such as stents and catheters, while preventing the stent's interior surfaces from receiving coating material.

2. Background of the Invention

Coatings are often applied to medical implants, such as pacemakers, vascular grafts, catheters, stents, heart valves, tissues or sensors to have desired effects and increase their effectiveness. These coatings may deliver a therapeutic agent to the lumen that reduces smooth muscle tissue proliferation or restenosis and may comprise a polymer carrier. Furthermore, implants may be coated to improve surface properties such as lubriciousness, to achieve enhanced biocompatibility and to control the timing and rate of release of the therapeutic agent being delivered. Balloon delivery systems, stent grafts and expandable stents are specific examples of implants that may be coated and inserted within the body. Stents such as described in U.S. Pat. No. 4,733,665 are tiny, expandable mesh tubes supporting the inner walls of a lumen used to restore adequate blood flow to the heart and other organs.

Conventionally, coatings are applied to the inner and outer surface of a stent in a number of ways, including, though not limited to, dip coating, dispensing or spray coating.

Applying a drug-containing coating uniformly on the inner and outer surface of the medical device can however lead to adverse drug effects or delivery to non-target tissue due to exposure of the coating material to the bloodstream. Additionally, it is desirable to coat only the outer surface of the stent to avoid excessive use of expensive coating material.

It is known to mask a device by placing a temporary sleeve over a portion of the medical device or by using a special fixture comprising masking means contacting the inner surface of the device to prevent the coating from coming in contact with the inner portion of the device. A drawback of such masking means is the high degree of surface contact between the stent and the masking means that may cause sticking of the masking means to the stent.

It is also known to use special fixtures having a polygonal shape that extend through the inner hollow section of the stent to cover its inner surface as depicted in FIG. 1. When using these fixtures there is a risk of coating defects, as illustrated in FIG. 1. Droplets 41 passing through the openings of the stent 1 may deposit on the fixture or on the inner surface of the stent 1. The excess coating material forms a film 43 on the surface of the holder that leads to coating material accumulation 44 on the contact points between fixture 6 and stent 1 resulting in inhomogeneous coatings and coating defects.

When the coated stent is removed from the fixture the stent may stick to the masking means and excess coating may remain on and/or between the struts or some of the coating may be removed from the stent leaving bare areas. Inhomogeneous coatings and uncoated areas on the stent surface may compromise the implant's effectiveness due to potential complications arising from an inhomogeneous distribution of the therapeutic agent at the target site.

Thus, conventional stent holding devices have several drawbacks that may result in increased manufacturing costs of stents and in coating defects as described above leading to time consuming inspection and product scrap. A repeatable process of selectively coating the outer surface of a stent may therefore not be ensured. Finally, stent holding devices known by the prior art are not designed to support and rotate multiple stents simultaneously to efficiently apply a coating to the stents.

Accordingly, a shortcoming of the conventional coating techniques is the inability to coat selectively and repeatably the outer surface of the stent, while preventing coating defects. Thus, there is a need for a system and method for efficiently applying a high quality coating only on the exterior surface of a stent, while preventing coating application on the interior surface and coating defects.

SUMMARY

One object is to provide a method and device of selectively coating the outer surface of a stent.

Another object is to provide a holding device that prevents accumulation of excess coating material on the inner and/or outer surface of the stent so that coating defects can be prevented.

Yet another object is to provide a holding device that securely holds the stent while contacting only a small portion of the inner surface of the stent.

A further object is to provide a method and an apparatus to support and to rotate several stents simultaneously and to efficiently apply a coating to the stents.

In one embodiment, a holding device is provided to support a stent during a coating process and to prevent coating deposition on the inner surface of the stent. The holding device comprises a first portion with at least two structures extending through the inner hollow section of the stent and contacting the inner surface of the stent at their tips, the structures being arranged so that an inner hollow section is formed and extending to a second portion where the structures are connected. The inner surface of the stent is shielded by the structures and the coating composition entering through the stent openings is directed by the structures to the inner hollow section where the coating composition is accumulated. In one or more embodiments, the structures have a vane-like shape. Rotary motion may be applied to the holding device to rotate the stent so that excess coating material is forced towards the inner hollow section of the holding device. Also, the second portion may comprise an inner hollow section having at least one opening for the flow off of the coating material. Furthermore, a third portion may be provided being connected to the vanes and located on the opposite side of the second portion.

In another embodiment, a method of coating a stent is provided comprising the following steps. In a first step, a stent is mounted on a holding device having at least two structures, which extend through the inner hollow section of the stent and contact the inner surface of the stent at their tips, and are arranged and shaped so that an inner hollow section is formed. Next, the holding device is rotated. In another step, the coating material is deposited onto the outer surface of the stent. Then, the coating material that enters the openings of the stent is directed towards the inner hollow section of the holding device so that deposition of coating material on the inner surface of the stent is prevented. In one or more embodiments, the step of disintegrating the coating material into a plurality of fine droplets, which may be directed by a gas stream towards the stent is furthermore provided. The coating material can be applied using a dispenser or may be disintegrated into a plurality of fine droplets using a spraying device.

In yet another embodiment, a holding arrangement for handling, supporting and transmitting rotary motion to at least one medical device is provided. The holding arrangement comprises a frame and at least one holding device, wherein the medical device is supported by the holding device and the holding device can be rotated in relation to the frame to rotate the medical device around its longitudinal axis. In one or more embodiments, the holding arrangement includes at least one shaft being rotable in relation to the frame to transmit rotary motion to at least one holding device. The holding device may comprise at least two structures, contacting the inner surface of the medical device at their tips while preventing coating deposition on the inner surface of the medical device.

In a further embodiment, an apparatus for rotating and coating to at least one medical device is provided. The apparatus comprises at least one lock member, a coating applicator and a detachable holding arrangement for handling and supporting at least one medical device. The holding arrangement includes a frame, at least a holding device that supports the medical device and can be rotated in relation to the frame. During rotation of the medical device a coating is applied and the frame of the holding arrangement is in contact with the lock member to secure the angular position of the holding arrangement, and during change of angular position of the holding arrangement the frame is not in contact with the lock member so that the holding arrangement can freely rotate. In one or more embodiments, linear motion is applied to the holding arrangement in order to translate the medical device. The apparatus may further comprise at least one motion unit to transmit motion to the holding arrangement. The coating applicator is preferably a spraying device, which disintegrates the coating composition into a plurality of fine droplets. The medical device is preferably a stent or a catheter.

In still another embodiment, a method for supporting, rotating and coating at least one medical device is provided, comprising the following steps. In a first step, the medical device is mounted to a detachable holding arrangement having a frame, at least a holding device, wherein the holding device can be rotated in relation to the frame. Then, the holding arrangement is secured at a first angular position and rotary motion is applied to the holding arrangement to rotate the medical device around its longitudinal axis. In a next step, a coating is applied to a medical device. In yet another step, the holding arrangement is indexed to the next angular position. Then, the holding arrangement is secured and rotary motion is applied to the holding arrangement to rotate the medical device around its longitudinal axis. In another step, a coating is applied to a medical device. In one or more embodiments, different coating layers are applied to the medical device at different angular positions. The same coating layer may be applied upon multiple medical devices and the medical devices are preferably stents.

DRAWINGS

The accompanying drawings, which are incorporated in and constitute a part of this specification, serve to explain the principles of the invention. The drawings are in simplified form and not to precise scale.

DETAILED DESCRIPTION

FIGS. 2-7 depict exemplary embodiments of the holding device of the present invention to securely support hollow cylindrical objects, such as stents and catheters, during the application of a coating. The holding device of the present invention comprises a portion consisting of at least two structures or vanes extending through the stent to one or two portions, also referred to as end portions, to connect the vanes and to be coupled to a shaft to rotate the stent. The vanes are arranged and shaped so that an inner hollow section is formed and the inner surface of the stent is shielded from receiving coating material. The contact area between the holding device and the stent has been limited to the pointed tips or edges of the vanes contacting the inner surface of the stent along the stent's length to prevent coating defects. The vanes are preferably designed to minimize the contact area between the stent and the holding device and to optimize the efficiency with which the fluid is directed inward towards the inner hollow section of the holding device.

Figure 1:
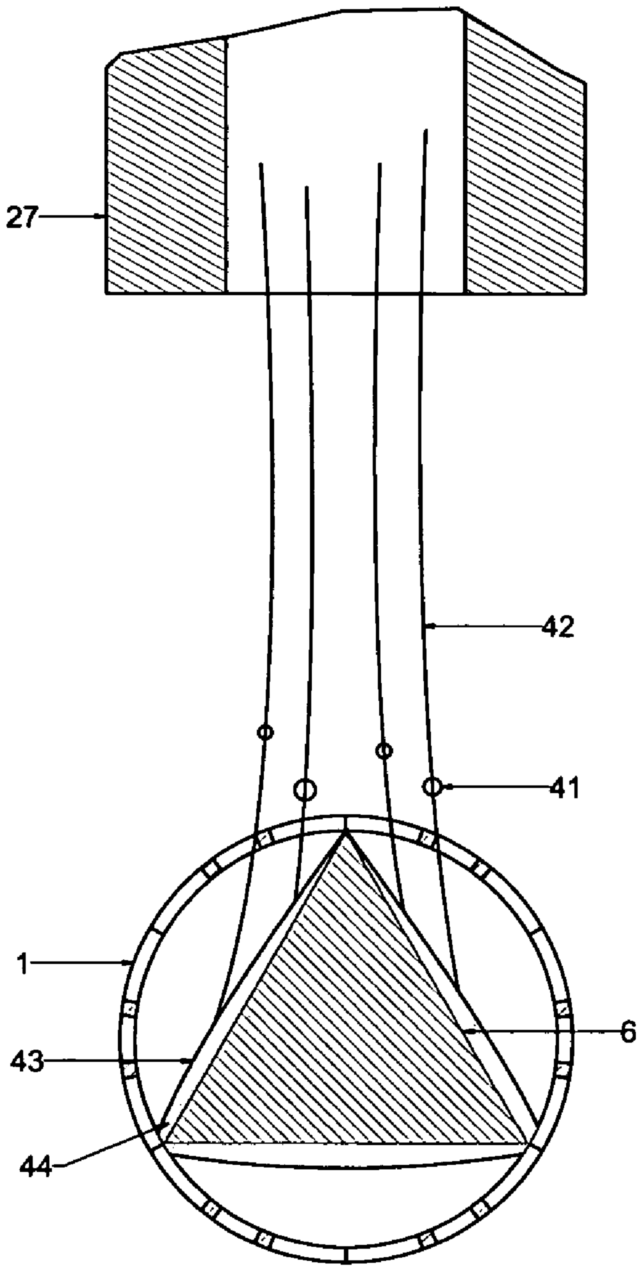
FIG. 1 PRIOR ART
FIG. 1 (Prior Art) is a cross-section front view showing a spray coating setup using a holding device known by the prior art.
Figure 2A:
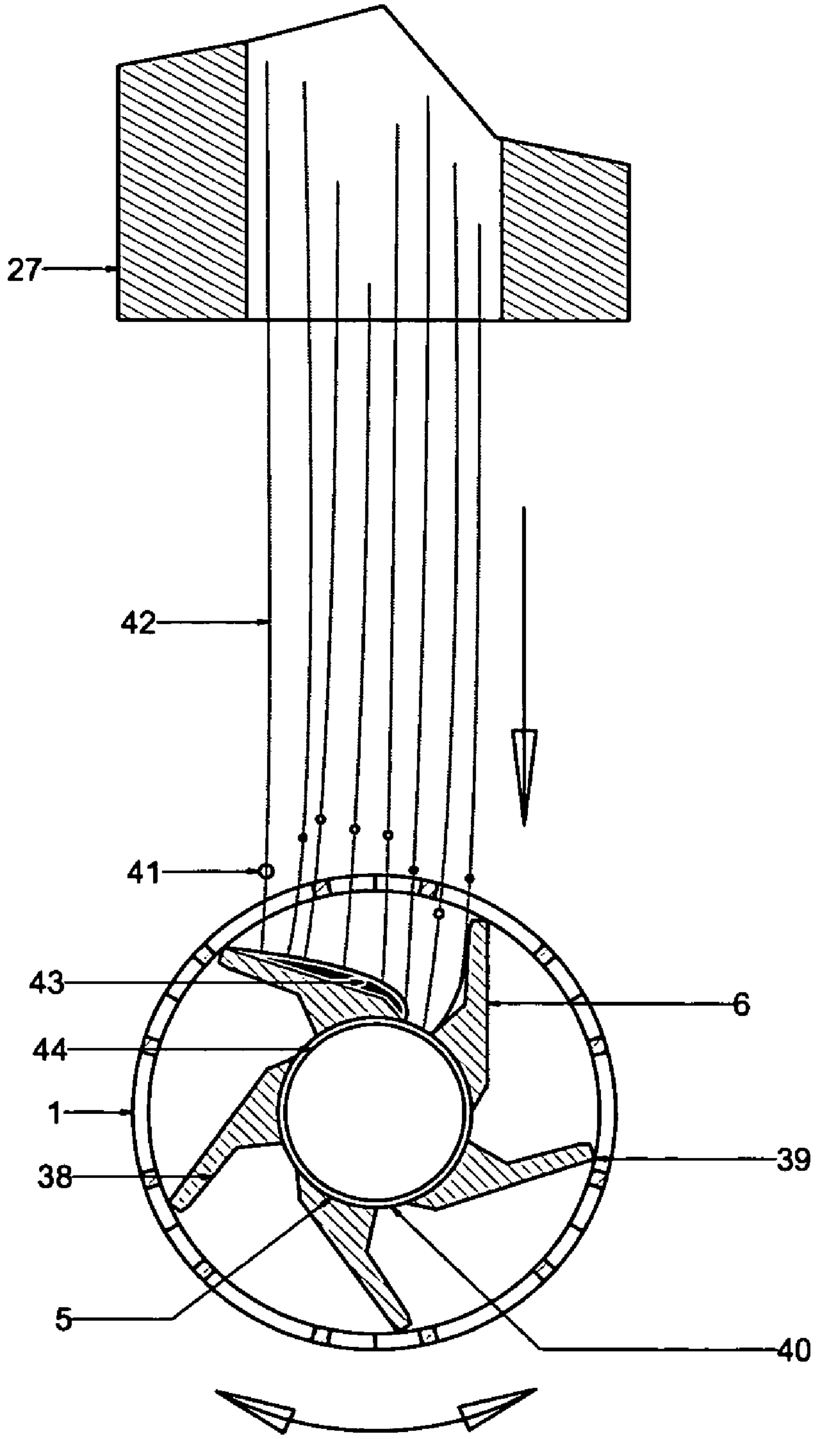
FIG. 2A is a longitudinal cross-section front view showing a spray coating setup using an rotor shaped holding device (holding device in horizontal orientation, atomizer located perpendicular to spray target)
Figure 2B:
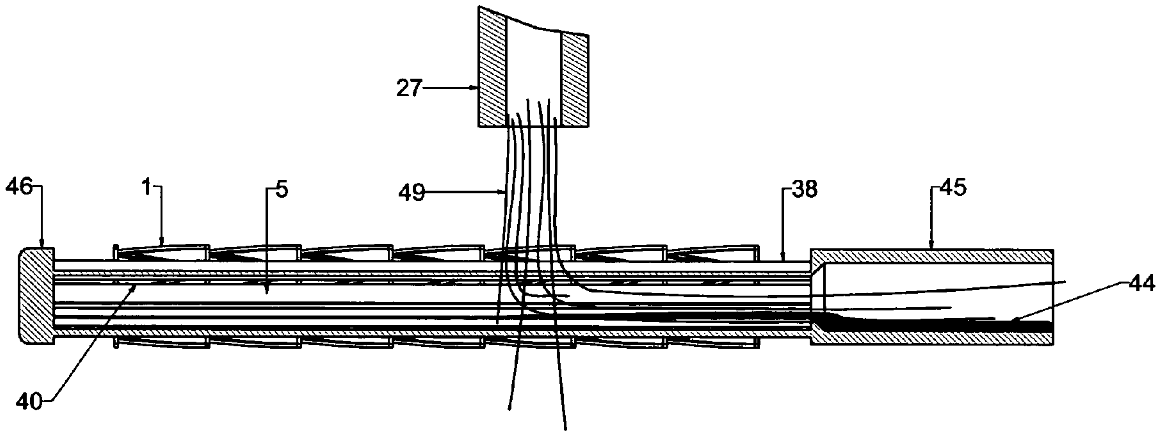
FIG. 2B is a cross-section front view of FIG. 2A.

Referring now to FIG. 2A and FIG. 2B, a coating setup to selectively coat a stent is provided. The exemplary holding device 6 that is used to secure stent 1 (shown in detail in FIG. 7) comprises several wing shaped profiles or vanes 38. The stent 1 is mounted on the holding device 6 by sliding the stent on the vanes. The vanes contact the inner surface of the stent 1 with their edges 39, so that the stent is securely held and the inner surface of the stent is shielded by the vanes 38. An atomizer 27 is positioned above the stent 1 and its spray axis is located on the same plane as the rotation axis of stent 1. Alternatively, a dispenser may be used to generate discrete droplets or a fluid stream. Means to produce a gas stream to transport the coating material to the stent are provided.

During operation, rotary motion is transmitted to the holding device 6 and the stent 1 is rotated. Atomizer 27 generates droplets 41, which are directed by the gas stream to the stent 1. The droplets 41 are deposited on the outer surface of the stent or penetrate through the openings between the struts into the inner hollow section of stent 1. Depending on droplet size, droplet velocity, impingement angle, and droplet trajectory 42 the droplets 41 may deposit on the vanes 38 or may pass through the spaces 40 between the vanes into the inner hollow section 5 of the holding device. The droplets 41 that are deposited on the vanes 38 form a film 43. The film 43 is directed by the gas stream and rotary motion towards the spaces 40 between the vanes into the inner hollow section 5 of the holding device where the excess coating material 44 is accumulated. The gas stream exits the holding device at the opening of end portion 45 and transports the excess coating material outside the holding device as shown in FIG. 2B. Thus, the excess coating material can flow off the holding device and may be collected in a separate container (not shown) resulting in minimized waste and facilitated cleaning of the holding device.

To decrease the coating time, several atomizers 27 may encircle stent 1 to apply the coating, thereby forcing the excess coating material into inner hollow section 5 of the holding device 6.

Figure 3A:
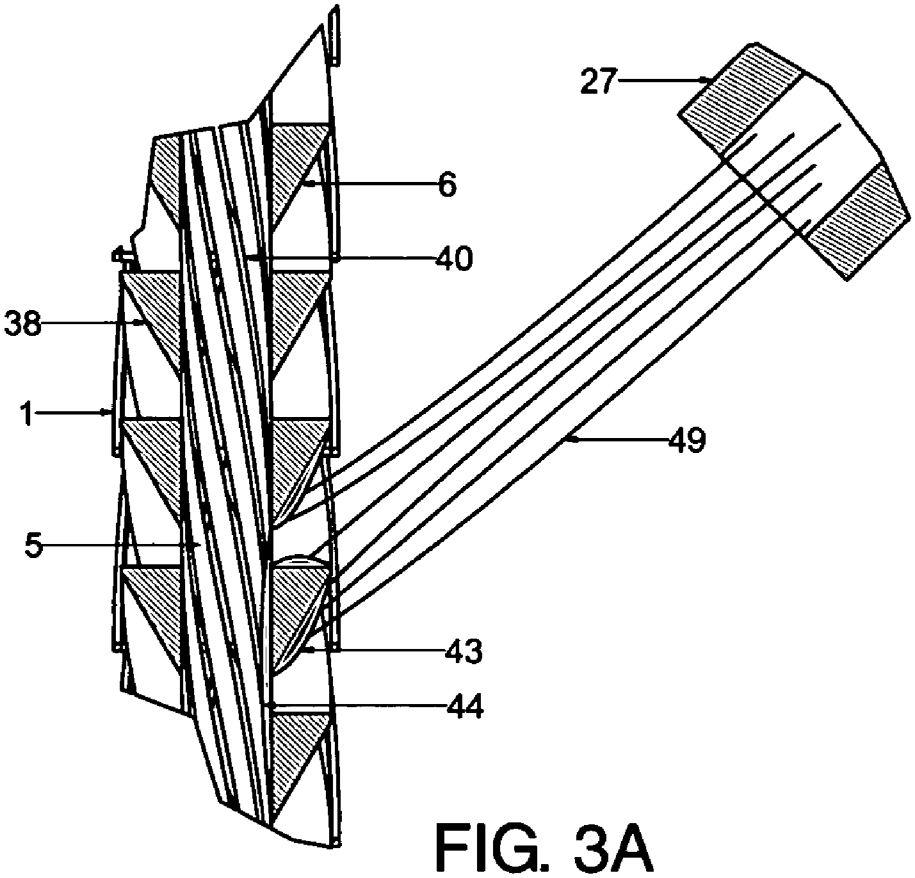
FIG. 3A is a cross-sectional front view showing a spray coating setup using a coil shaped holding device comprising vanes (holding device in vertical orientation, atomizer located at an angle in relation to spray target)
Figure 3B:
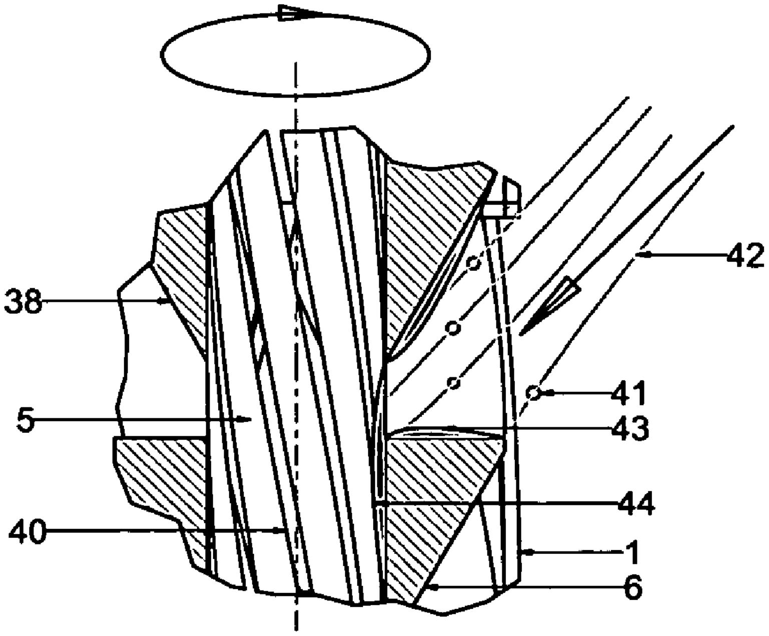
FIG. 3B is a detailed view of the holding device of FIG. 3A.

Another exemplary coating setup using an alternative holding device is provided in FIG. 3A and FIG. 3B. The holding device 6 (shown in detail in FIG. 4A and FIG. 4B) comprises several tapered vanes twisted along its longitudinal axis. Stent 1 is mounted on the edges 39 of the vanes 38. The holding device 6 is placed in a vertical orientation. The spray axis of the atomizer 27 is located in the same plane as the longitudinal axis of the holding device 6 and is tilted in relation to the holding device so that the droplet trajectories are parallel to the tapered profiles of the vanes. Means to produce a gas stream 49 to transport the coating material to the stent are provided.

During operation, rotary motion is applied to the holding device 6 and the stent 1 is rotated around its longitudinal axis. The atomizer 27 generates droplets 41 that are directed by the gas stream 49 to the stent 1. The droplets 41 deposit on the stent's outer surface or penetrate through the openings between the struts of the stent 1. Depending on droplet size, droplet velocity, impingement angle, and droplet trajectory 42 the droplets 41 entering through the openings of the stent may pass through the spaces 40 formed between the vanes into the inner hollow section 5 of the holding device or may deposit on the vanes 38. The droplets 41 that deposit on the vanes 38 form a film which is forced through the spaces 40 between the vanes towards the inner hollow section 5 of the holding device 6 where the excess coating material is accumulated.

FIGS. 4 to 7 represent longitudinal and cross-sectional views of exemplary embodiments of the holding device. The holding device comprises a portion being inserted into the hollow section of the stent having at least two structures, also referred to as vanes or profiles. The structures extend to two end portions, where the vanes are connected, and may be coupled to a shaft to rotate the stent. The end portions may have a polygonal, hemispherical or cylindrical shape and may comprise an inner hollow section with one or more openings. To facilitate stent mounting the edges of the end portions are preferably rounded or tapered. The portion contacting the inner surface of the stent has a diameter that is sufficiently sized to provide a stable connection during transmission of rotary motion to the stent and to prevent slipping of the stent. The vanes may be curved or flat, of constant or varying thickness, have an identical or varying curvature, and have a constant or varying spacing between them. The stent holding device can be made from a suitable metallic material such as stainless steel, titanium, cobalt chromium alloys, or a polymeric material such as PEEK. The holding device may be made from one piece, for example by machining a hollow blank or a tube. Alternatively, the holding device may be comprised of several parts. For example, the vanes may be made from sheets and mounted to one or more connectors comprising pockets to secure the sheets.

Figure 4A:
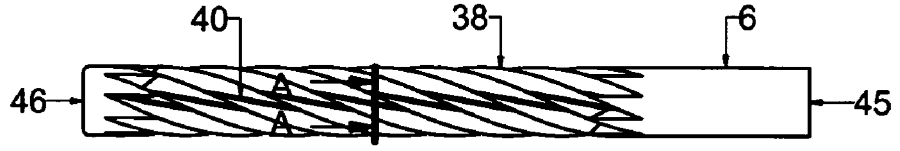
FIG. 4A is a longitudinal view showing a holding device comprising twisted vanes.
Figure 4B:
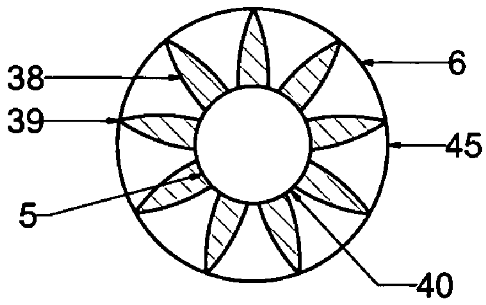
FIG. 4B is a cross-section front view of FIG. 4A.

With reference to FIG. 4A, a longitudinal representation of an exemplary holding device 6 is provided. It comprises a first end portion 45 to be connected to a drive shaft (not shown), a portion consisting of slightly twisted vanes 38 to be inserted into a stent (not shown) and a second end portion 46, which is slightly rounded. FIG. 4B is a cross-sectional view of the holding device. The vanes 38 are arranged and shaped so that a comparatively large inner hollow section 5 is formed where excess coating material can accumulate. The vanes 38 are arranged in a circular pattern and comprise spaces 40 there between for the passage of the excess coating material into inner hollow section 5 of the holding device.

Figure 5A:
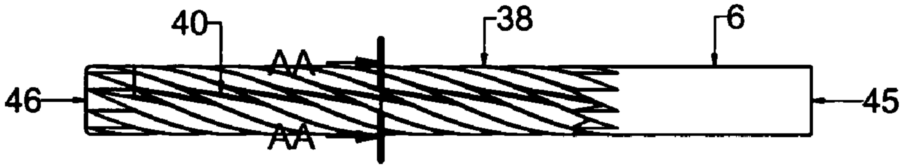
FIG. 5A is a longitudinal view showing a holding device comprising twisted and curved vanes.
Figure 5B:
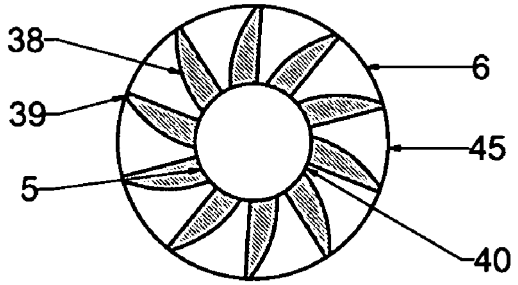
FIG. 5B is a cross-section front view of FIG. 5A.

FIG. 5A and FIG. 5B is a variation of the holding device 6 depicted in FIG. 4A and FIG. 4B having curved vanes 38.

Figure 6A:
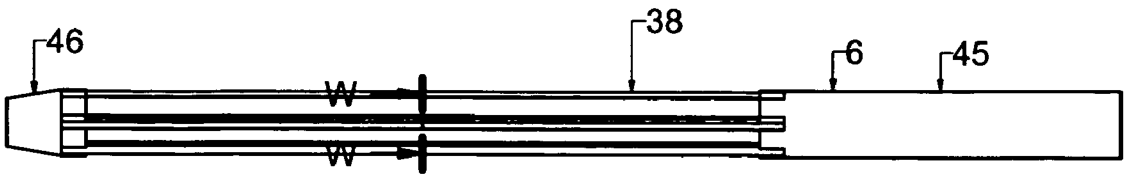
FIG. 6A is a longitudinal view showing a holding device comprising flat vanes.
Figure 6B:
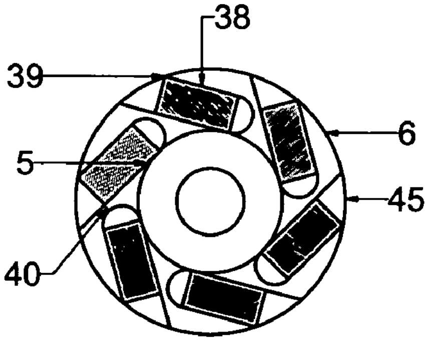
FIG. 6B is a cross-section front view of FIG. 6A.

Another exemplary holding device having a modular structure is shown in FIG. 6A and FIG. 6B. Referring to FIG. 6A, the holding device includes two members 45, 46 or connectors at both ends to arrange and to secure the vanes 38. Member 46 to be inserted into the stent (not shown) has a chamfered edge to facilitate mounting and member 45 may be coupled to a drive shaft (not shown) to rotate the stent. The vanes 38 are arranged around the longitudinal axis of the holding device as shown in FIG. 6B. When a stent is mounted on the holding device 6, the inner surface of the stent is contacted at one edge 39 of each vane 38. The vanes 38 shield the entire inner surface of the stent and are arranged and shaped so that a space 40 is provided between each vane to allow excess coating material to enter inner hollow section 5.

Figure 7A:
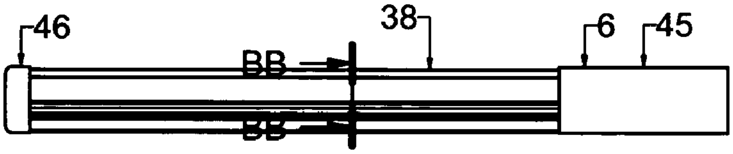
FIG. 7A is a longitudinal view showing a holding device comprising tapered vanes.
Figure 7B:
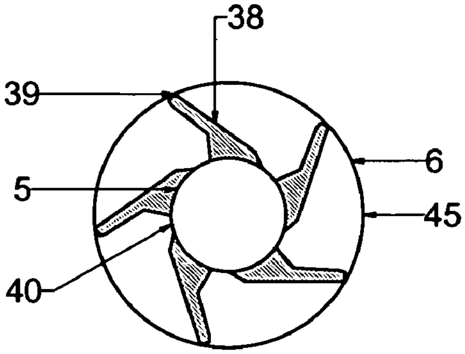
FIG. 7B is a cross-section front view of FIG. 7A.

FIG. 7A is a longitudinal representation of a further exemplary holding device. The vanes 38 extend on one side to end portion 45, which may be coupled to a drive shaft (not shown), to apply rotary motion to a stent (not shown), and on the other side to end portion 46 having rounded edges. The vanes 38 are symmetrically arranged around the longitudinal axis of the holding device 6 and arranged so that a comparatively large inner hollow section 5 is provided. FIG. 7B is a cross-sectional view of the holding device illustrated in FIG. 7A.

Figure 8:
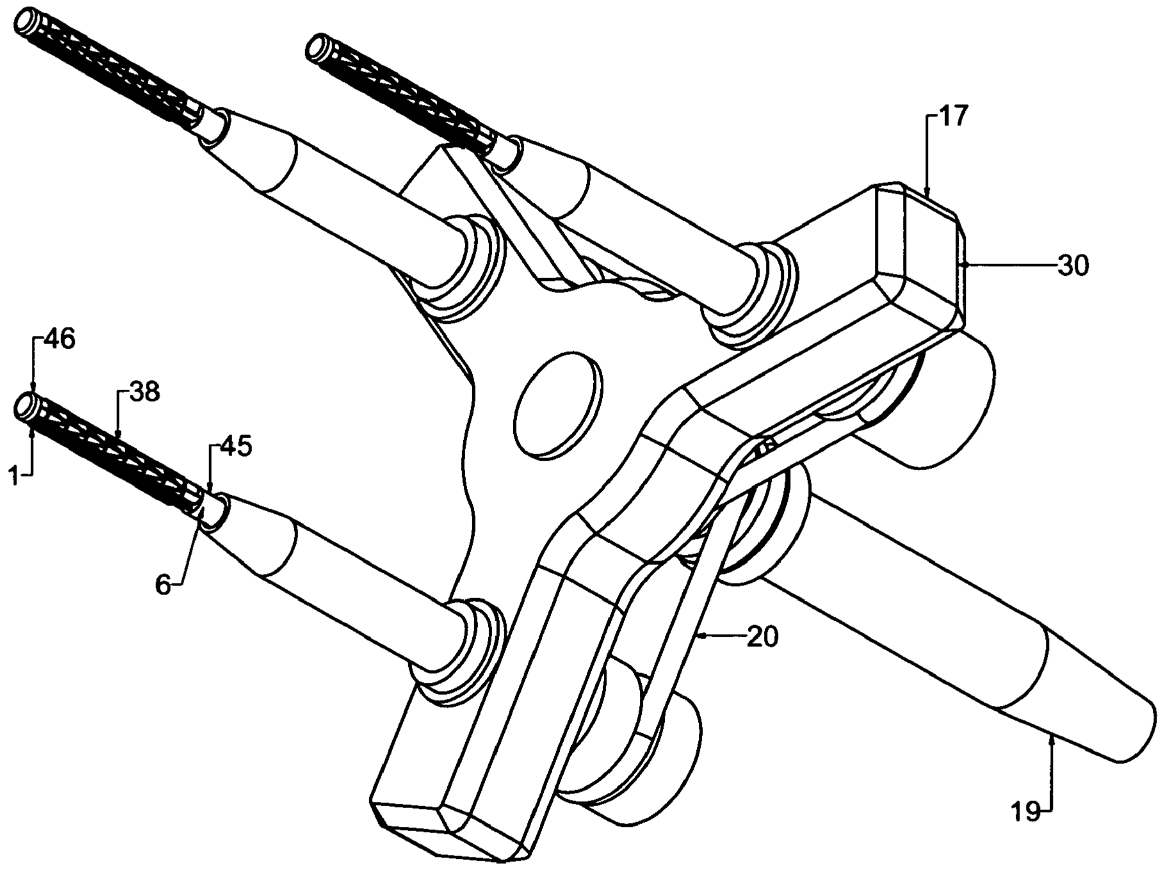
FIG. 8 is an isometric view of a holding device arrangement for selectively coating at least one stent.

To allow higher volume production of stents, it is desirable to have a holding apparatus that supports and rotates several stents and allows efficiently coating of multiple stents. An isometric representation of an exemplary holding arrangement 30 to secure and to apply rotary motion to up to three stents is depicted in FIG. 8. The holding arrangement 30 includes frame 17, shaft 19 and three holding devices 6, which are engaged with the inner section of the stent 1 at the vanes 38. The shaft 19 and the holding devices 6 are bearing mounted to the frame 17. The holding devices 6 are connected 260 with belts 20 to shaft 19. Rotary motion is induced in shaft 19 and transmitted to the holding devices 6 to rotate the stents simultaneously. The holding arrangement can be equipped with a larger frame to accommodate six holding devices 6 to support up to six stents.

When coating other tubular devices, such as catheters, the holding arrangement is preferably vertically oriented, so that the catheters can hang from the frame. Each medical device is preferably supported by a holding device contacting at least partially the inner section of the medical device.

Figure 9:
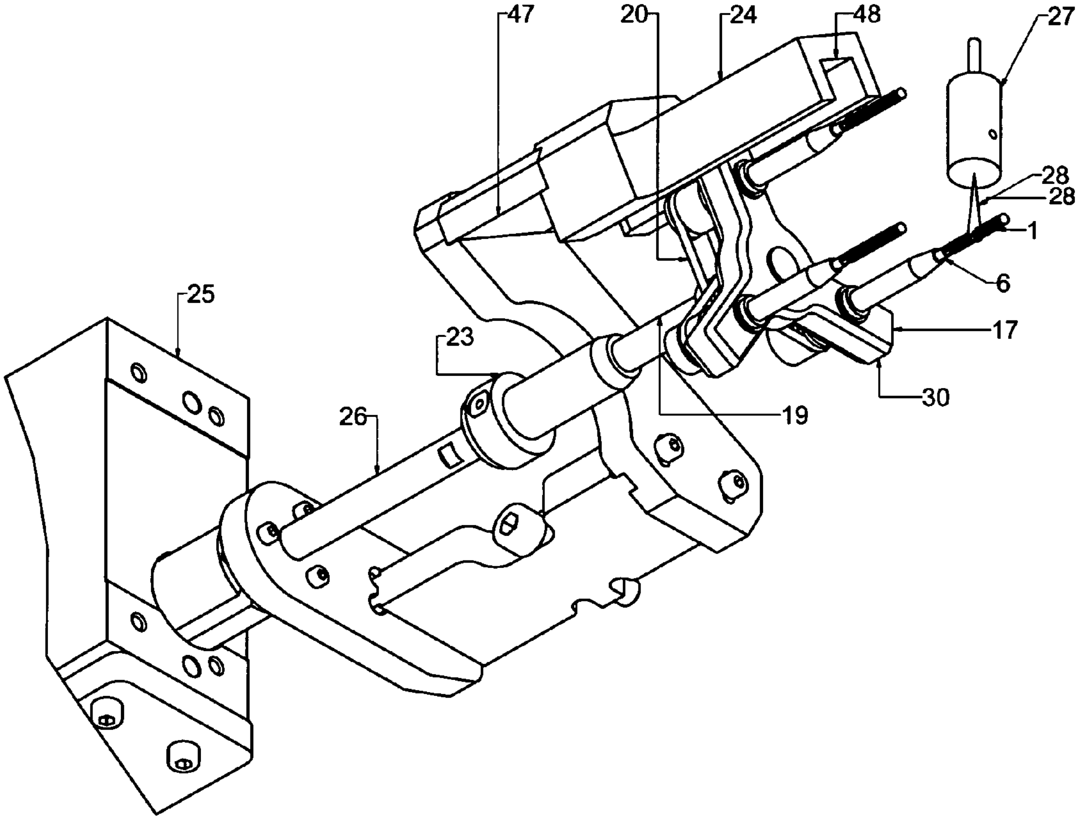
FIG. 9 is an isometric view of an apparatus for coating at least one stent.

FIG. 9 illustrates an exemplary stent holding apparatus and a method of efficiently coating multiple stents. Three stents 1 are supported by the holding arrangement 30 of the present invention and an atomizer 27 is provided to apply a coating composition to one stent at a time. The holding arrangement 30 (described in detail in FIG. 8) is connected via coupling 23 to the drive shaft 26 of motion unit 25 and is in contact with guide member 24, which prevents unwanted indexing of the holding arrangement 30 and secures it. The frame 17 aligns the holding arrangement 30 in relation to the guide member 24. The drive shaft 26 is preferably equipped with an automated coupling element 23 to easily connect the shaft 19 to the drive shaft 26.

During the application of the coating, rotary and linear motion is applied via drive shaft 26 to the holding arrangement 30. Rotary motion is induced via shaft 19, belts 20 and holding devices 6 to rotate the stents 1. The holding arrangement 30 is moved in a linear direction relative to the atomizer 27 generating spray plume 28 and the stents 1 are rotated. The atomizer 27 is preferably aligned in relation to the stent 1, so that the center axis of the spray plume 28 is perpendicular to the rotation axis of stent 1 and both axes are located on the same plane. After coating the first stent, the holding arrangement 30 is moved to the backward position 47 to disconnect it from guide member 24 so that the frame 17 can be freely rotated. The motion unit 25 indexes the holding arrangement 30 at 120 degrees and the coating can be applied to the next stent.

After coating all supported devices another process step may be performed, such as applying a different coating layer or performing a drying operation.

Alternatively, the holding arrangement may be dismounted to continue with the optical inspection of the coated medical devices. The holding arrangement 30 is moved to the forward position 48, uncoupled from coupling 23 and removed from drive shaft 26 and guide member 24. An exemplary inspection setup may comprise guide members, linear stage and an inspection apparatus like a microscope. By turning shaft 19 of the holding arrangement 30, the stent may be rotated to inspect 290 the coating. Thus, it is not required to dismount and remount the stents for inspection purposes or to use inspection fixtures, which may damage the outer surface of the stent. Coating damages during handling and inspection can therefore be prevented or minimized resulting in savings in time and cost.

The method for efficiently applying one or more coating layers to multiple medical devices using the apparatus shown in FIG. 9 is described in more detail below. First, the medical devices are mounted to the holding arrangement comprising a frame, holding devices and at least a shaft. The holding devices and the shaft can be rotated in relation to the frame and rotary motion is transferred between the shaft and the holding device. Next, the holding arrangement is detachably coupled to a motion unit to rotate and translate the medical devices that are supported by the holding arrangement. In a further step, the holding arrangement is secured at a determined angular position, so that the first medical device is located in the coating area in vicinity to the first coating applicator. Rotary motion is applied to the holding arrangement to rotate the medical device around its longitudinal axis. Then, the coating is applied to the first medical device. After application of the coating, the holding arrangement is indexed to the next angular position and the second medical device is located in the coating area in vicinity to the second coating applicator. In another step, the coating is applied to the second medical device.

Further coating layers may be applied as described above at a variety of angular positions. Depending on the particular application, the coating sequence may be repeated or other process steps like drying can be performed.

In a further embodiment, one or more process steps may be performed simultaneously for all supported devices.

In still another embodiment one medical device may be mounted to the apparatus and several process steps, such as different coating layers, may be performed automatically at various angular positions.

Figure 10:
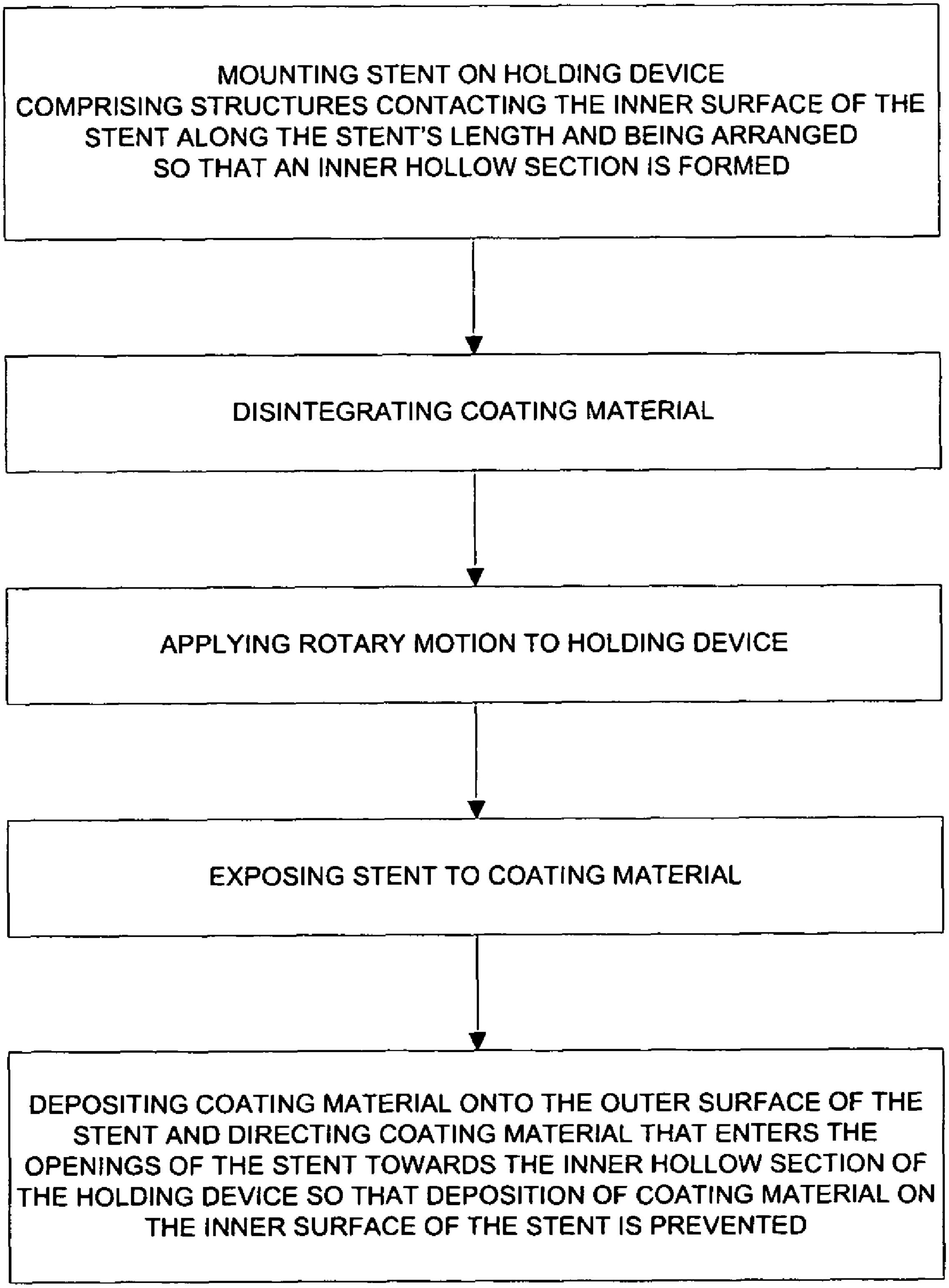
FIG. 10 is a flow chart of the method of selectively coating the outer surface of a stent.

Referring to FIG. 10, the method of selectively coating a hollow tubular body, such as a stent, includes the steps of mounting a stent on a holding device having at least two structures that contact the inner surface of the stent along the stent's length at their tips and being arranged and shaped so that an inner hollow section is formed, disintegrating the coating material, rotating the holding device, exposing the stent to the coating material, depositing the coating material onto the outer surface of the stent, and directing the coating material that enters the openings of the stent towards the inner hollow section of the holding device, so that deposition of coating material on the inner surface of the stent is prevented.

Figure 11A:
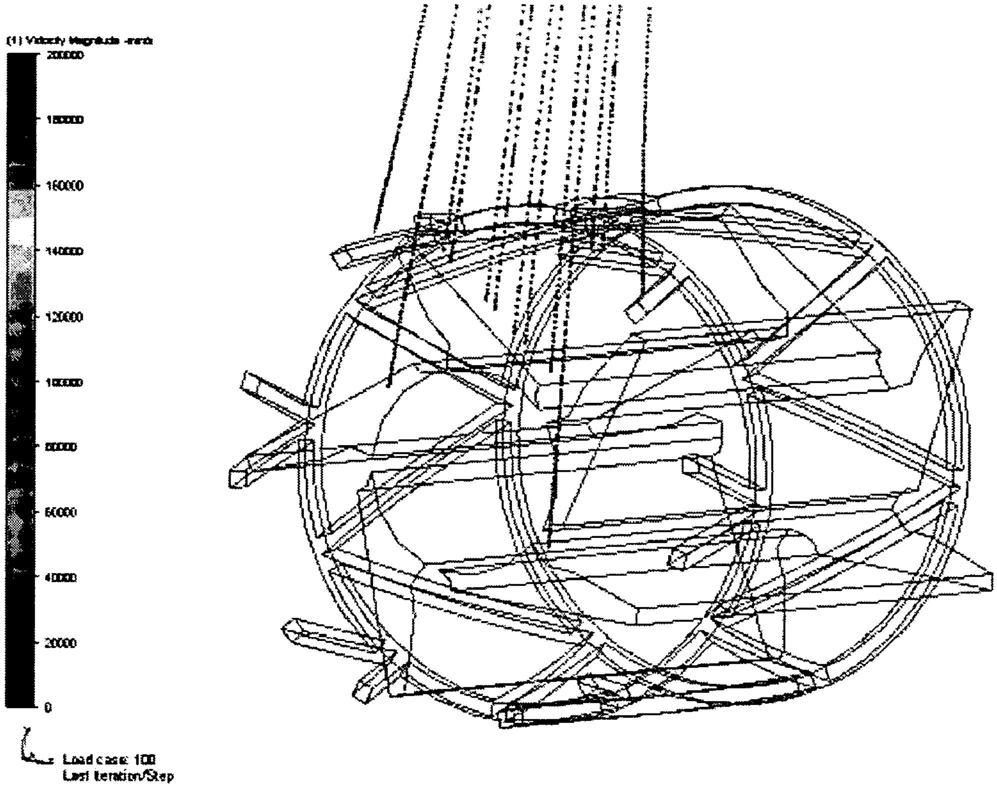
FIG. 11A is an isometric view of the holding device showing the droplet trajectories during a selective coating process.
Figure 11B:
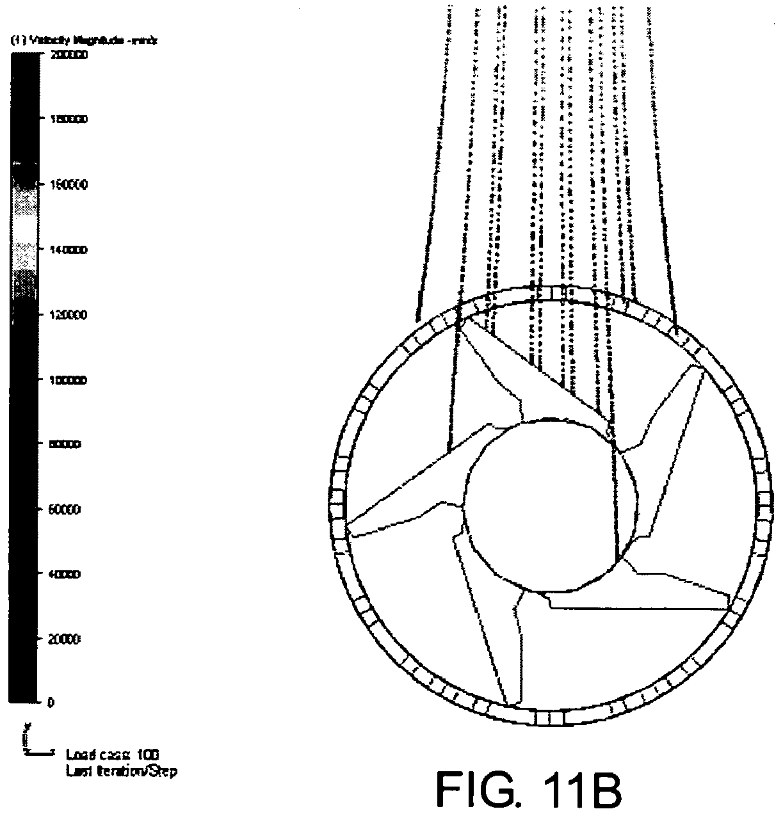
FIG. 11B is a front view of the holding device shown in FIG. 11A.

FIG. 11A and FIG. 11B represents a Computation Fluid Dynamics (CFD) simulation of droplet trajectories (shown by dotted lines) and deposition during the spray coating process described below using the holding device shown in FIG. 7 and the method described above. The atomizer orifice is positioned approximately 10 mm above the stent. The droplets produced by the atomizer having a size of approximately 6 μm are transported within the gas stream towards the stent 1. One can see that the droplets are deposited on the outside surface of the stent or penetrate the stent 1 structure and are deposited on the vanes 38. The droplets form a film onto the vanes 38 which is forced by the gas stream and the rotary motion of the holder 6 through the spaces 40 into inner hollow section 5 of the holding device. The inner surface of the stent 1 is shielded by the vanes 38, thereby preventing deposition of droplets on the stent's inner surface. An accumulation on the contact points between the stent and the holding device and a deposition on the inner surface of the stent is prevented.

Stent Coating Example Using the Apparatus of the Present Invention

The following method of selectively coating one or more stents using the holding device of the present invention is being provided by way of illustration and is not intended to limit the embodiments of the present invention.

Stents (manufactured by STI, Israel) having a diameter of 3 mm and a length of 20 mm may be coated. The coating composition may include a solvent capable of dissolving the polymer at the concentration desired in the composition, a non-bioabsorbable or bioabsorbable polymer that can be dissolved in the composition, and a therapeutic substance. The composition can also include active agents, radiopaque elements, or radioactive isotopes.

The coating composition may comprise a solvent, a polymer, and a therapeutic substance. The therapeutic substance may include, but is not limited to, proteins, hormones, vitamins, antioxidants, antimetabolite agents, anti-inflammatory agents, anti-restenosis agents, anti-thrombogenic agents, antibiotics, anti-platelet agents, anti-clotting agents, chelating agents, or antibodies. Examples of suitable polymers include, but are not limited to, synthetic polymers including polyethylen (PE), poly(ethylene terephthalate), polyalkylene terepthalates such as poly(ethylene terephthalate) (PET), polycarbonates (PC), polyvinyl halides such as poly(vinyl chloride) (PVC), polyamides (PA), poly(tetrafluoroethylene) (PTFE), poly(methyl methacrylate) (PMMA), polysiloxanes, and poly(vinylidene fluoride) (PVDF); biodegradable polymers such as poly(glycolide) (PGA), poly(lactide) (PLA) and poly(anhydrides); or natural polymers including polysaccharides, cellulose and proteins such as albumin and collagen. The coating composition can also comprise active agents, radiopaque elements or radioactive isotopes. The solvent is selected based on its biocompatibility as well as the solubility of the polymer. Aqueous solvents can be used to dissolve water-soluble polymers, such as Polyethylene glycol) (PEG) and organic solvents may be used to dissolve hydrophobic and some hydrophilic polymers. Examples of suitable solvents include methylene chloride, ethyl acetate, ethanol, methanol, dimethyl formamide (DMF), acetone, acetonitrile, tetrahydrofuran (THF), acetic acid, dimethyle sulfoxide (DMSO), toluene, benzene, acids, butanone, water, hexane, and chloroform. For the sake of brevity, the term solvent is used to refer to any fluid dispersion medium whether a solvent of a solution or the fluid base of a suspension, as the invention is applicable in both cases.

Three stents are mounted to the holding arrangement depicted in FIG. 8. After mounting the stents, the holding arrangement is removably connected to the motion unit of the present invention shown in FIG. 9 to rotate and translate the stents supported by the holding arrangement. The angular position of the holding arrangement is secured by a guide member, so that the first stent is located in the coating area in vicinity to the coating applicator.

A pneumatic atomizer is provided to disintegrate the coating composition into fine droplets. Alternatively, other types of atomizers, such as ultrasonic nozzles comprising pneumatic means for droplet transport can also be employed for the application of the composition. The spray nozzle can disintegrate the coating solution into fine droplets at a liquid flow rate of about 0.1 to 80 ml/h and an atomizing pressure ranging from about 0.5 bar to about 1.5 bar. The nozzle is preferably operated at a liquid flow rate of 5 ml/h, at an atomizing gas flow rate of 5 l/min and at an atomizing pressure of 0.8 bar. Droplets having a volumetric median diameter between 2 and 7 microns and a largest droplet diameter of less than 20 microns are produced. The atomizer may be aligned in relation to the stent, which is located in the coating area, so that the spray axis of the atomizer is perpendicular to the rotation axis of the stent and both axes are in the same plane. The spray nozzle is preferably adjusted to provide a distance from the nozzle tip to the outer surface of the stent of 10 to 35 mm. A syringe pump, which may be operated at a constant flow rate of approximately 5 ml/h, can be used to feed the liquid to the atomizer during the application of the coating.

Rotary motion is transmitted from the motion unit to the holding arrangement to rotate the supported medical device around its longitudinal axis. Translational motion is transmitted to the holding arrangement to move it in a linear direction along the guide member in relation to the spray nozzle so that the first stent is exposed to the spray.

During the application of the coating solution, rotary motion is transmitted from the drive shaft of the motion unit to the holding arrangement to rotate the stent about its central longitudinal axes. The rotation speed of the stent can be from about 5 rpm to about 250 rpm. By way of example, the stent may rotate at 130 rpm. Alternatively, the stent can be translated along its central longitudinal axes. The translation speed of the stent can be from about 0.2 mm/s to 8 mm/s. When applying the coating solution, the translation speed is preferably 0.5 mm/s.

The stent can be moved along the nozzle one time to apply the coating in one pass or several times to apply the coating in several passes. Alternatively, the nozzle may be moved one time or several times along the stent length. The flow rate of the coating solution may range from about 1 ml/h to 50 ml/h, and is preferably 5 ml/h.

After coating the first stent, the holding arrangement is moved to the backward position. The frame is not any more in contact with the guide member and can freely rotate to index the holding arrangement by 120 degrees so that the next stent is placed in the coating area.

After coating all supported stents, the holding arrangement may be detached form the coating apparatus to inspect the stents.

While the invention will be described in connection with certain embodiments, it will be understood that the invention is not limited to these embodiments. On the contrary, the invention includes all alternatives, modifications and equivalents as may be included within the spirit and scope of the present invention. Details in the Specification and Drawings are provided to understand the inventive principles and embodiments described herein, to the extent that would be needed by one skilled in the art to implement those principles and embodiments in particular applications that are covered by the scope of the claims.

The invention claimed is:

1. A method of coating a stent, comprising the steps of:

mounting the stent on a holding device having at least two structures that are located circumferentially around the longitudinal axis of the holding device entirely extend through the inner hollow section of the stent and contact the inner surface of the stent along the stent length at their tips and which are arranged and shaped so that an inner hollow section is formed there between;

rotating the holding device;

depositing the coating material onto the outer surface of the stent; and directing the coating material that enters openings of the stent towards the inner hollow section of the holding device so that deposition of coating material on the inner surface of the stent is prevented.

2. The method according to claim 1, wherein the holding device comprises a first portion with at least two structures extending through the inner hollow section of the stent and a second portion where the structures are connected, and wherein the inner surface of the stent is shielded by the structures and the coating material entering through the stent openings is directed by the structures to the inner hollow section where the coating composition is accumulated.

3. The method according to claim 2, wherein the structures of the holding device are shaped in such a way that the structures are capable of directing the coating composition entering through the stent openings to the inner hollow section.

4. The method according to claim 1, wherein during the rotation step excess coating material is forced towards the inner hollow section of the holding device.

5. The method according to claim 2, wherein the second portion of the holding device comprises an inner hollow section having at least one opening for the flow off of the coating material.

6. The method according to claim 2, further comprising a third portion connected to the first portion and located on the opposite side of the second portion.

7. The method according to claim 1, further comprising the step of disintegrating a coating material into a plurality of fine droplets.

8. The method according to claim 7, wherein the droplets are directed by a gas stream towards the stent.

9. The method according to claim 1, wherein the coating material is applied using a dispenser.

10. The method according to claim 1, wherein the coating material is disintegrated into a plurality of fine droplets using a spraying device.

11. The method according to claim 1, wherein the holding device is part of a holding arrangement comprising a rigid frame and the holding device can be rotated in relation to the frame to rotate the medical device around its longitudinal axis.

12. The method according to claim 11, wherein the holding arrangement further comprises at least one shaft that can be rotated in relation to the frame to transmit rotary motion to at least one holding device.

13. The method according to claim 11, wherein the holding device comprises at least two structures contacting the inner surface of the medical device at their tips while preventing coating deposition on the inner surface of the medical device.

14. Method for supporting, rotating and coating at least one medical device, comprising the steps of:

mounting the medical device to a detachable holding arrangement having a frame and at least a mandrel, wherein the medical device is mounted to the mandrel that can be rotated in relation to the frame;

securing the holding arrangement at a first angular position and applying rotary motion to the holding arrangement to rotate the medical device around its longitudinal axis at a first angular position;

applying a coating to the medical device;

indexing the holding arrangement to a next angular position that is different from the first angular position;

securing the holding arrangement and applying rotary motion to the holding arrangement to rotate the medical device around its longitudinal axis at the next angular position; and applying a coating to the medical device.

15. The method according to claim 14, wherein different coating layers are applied to the medical device at different angular positions.

16. The method according to claim 14, wherein the same coating layer is applied at different angular positions.

17. The method according to claim 14, wherein the medical device is a stent.

* * * * *